United States Patent [19]

Petit et al.

[11] Patent Number: 5,034,363
[45] Date of Patent: Jul. 23, 1991

[54] CATALYST OF THE GALLIUM-CONTAINING ALUMINOSILICATE TYPE AND ITS UTILIZATION IN THE AROMATIZATION OF LIGHT $C_2$-$C_4$ GASES

[75] Inventors: Laurent Petit, Paris; Jean-Paul Bournonville, Cergy Pontoise; Jean-Louis Guth, Mulhouse; Francis Raatz, Acheres; Henri Kessler, Wittenheim, all of France

[73] Assignee: Institut Francais du Petrol, Rueil-Malmaison, France

[21] Appl. No.: 379,468

[22] Filed: Jul. 12, 1989

[30] Foreign Application Priority Data

Jul. 12, 1988 [FR] France ............................ 88 09632

[51] Int. Cl.⁵ ............................................. B01J 29/04
[52] U.S. Cl. .......................................................... 502/61
[58] Field of Search ............................. 502/60, 61, 64

[56] References Cited

U.S. PATENT DOCUMENTS 4,520,118  5/1985  Gane et al. ............................ 502/61

FOREIGN PATENT DOCUMENTS 119023  9/1984  European Pat. Off. ............... 502/61

Primary Examiner—Carl F. Dees
Attorney, Agent, or Firm—Millen, White & Zelano

[57] ABSTRACT

An aluminosilicate type catalyst and its use in the aromatization of a $C_2$-$C_4$ light-gas cut in the presence or not of olefins is described.

The catalyst is characterized by the following composition expressed by weight:
a) 0.01 to 10% by weight of gallium
b) 0.1 to 99.49% of a matrix
c) 0.5 to 99.99% of a zeolite having the following approximate chemical formula:

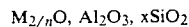

$$M_{2/n}O, Al_2O_3, xSiO_2$$

wherein
M represents a proton and/or a metallic cation,
n is the valency of said cation,
x is a number ranging from 12 to 1000,
said zeolite having a MFI structure being synthesized, moreover, in a fluoride medium and having a fluorine content ranging from 0.02 to 1.5% by weight incorporated during synthesis.

10 Claims, 1 Drawing Sheet

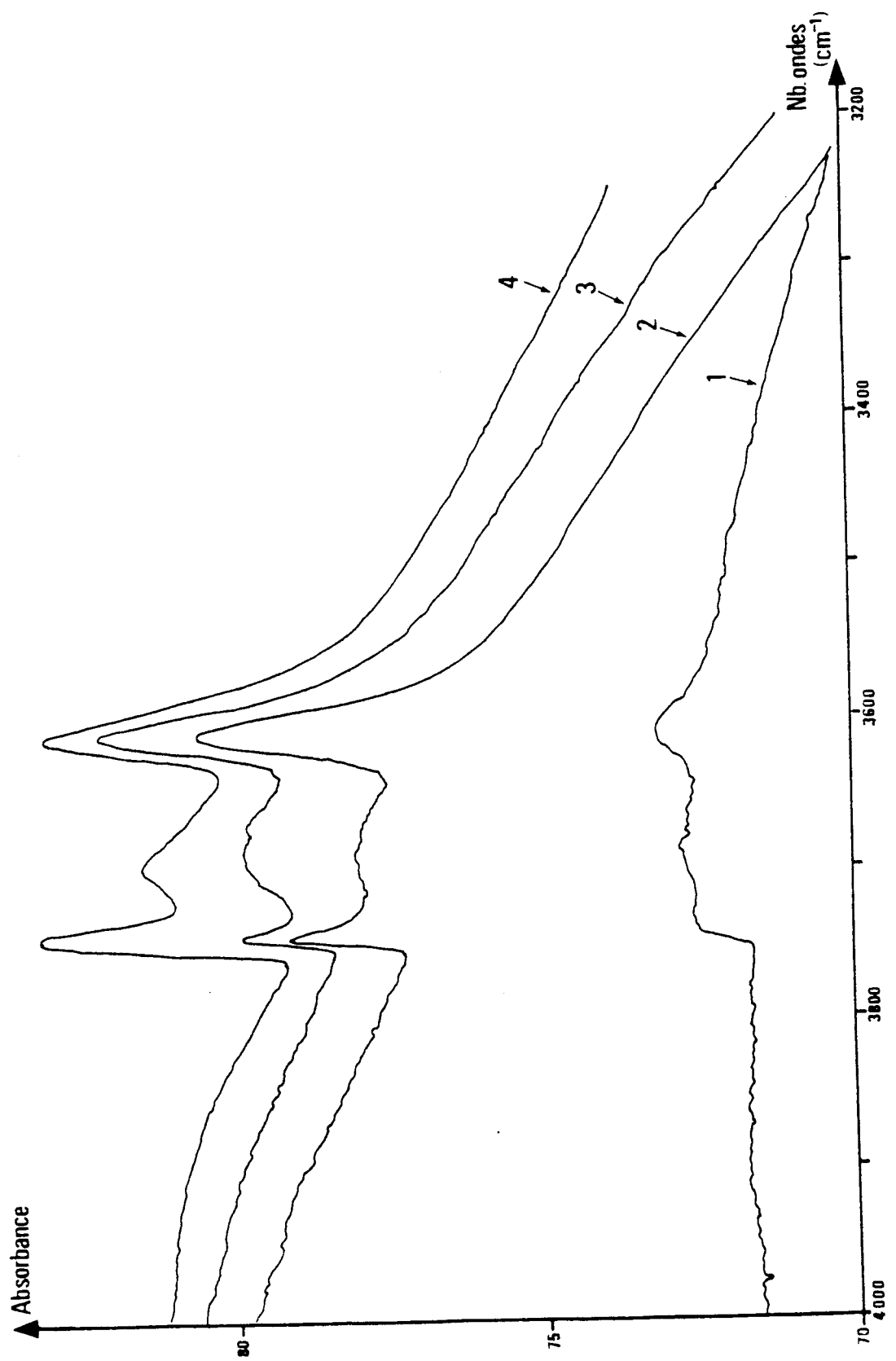

CATALYST OF THE GALLIUM-CONTAINING ALUMINOSILICATE TYPE AND ITS UTILIZATION IN THE AROMATIZATION OF LIGHT $C_2$-$C_4$ GASES

The present invention relates to:
an aluminosilicate type catalyst comprising a zeolite having an MFI structure, synthesized in a fluoride medium, containing silica, aluminium and gallium, and
use of this catalyst in the aromatization reactions of light-gas cuts having $C_{2-4}$- carbon atoms per molecule, in the optional presence of olefins.

The synthesis in fluoride media of this type of zeolite having a MFI structure has already been described in French patent No. 2567868 and, more recently, in an article by J. L. GUTH et al. (Proc. 7th Int. Zeolite Conf., Tokyo, August 1986, p. 121).

This synthesis involves:
a) in a first step, forming a reaction medium comprising water, a silicon source, an alumina source, a structuring agent source able to provide organic cations chosen from the group constituted by tetrapropylammonium ions (TPA+) and tetrapropylphosphonium ions (TPP+), this reaction medium further containing fluoride anions. The pH of the medium is generally less than 10 and the molar ratios of the various constituents of the reaction medium are described in French patent No. FR2567868,
b) in a second step, in heating said reaction medium formed step (a) to a temperature ranging from about 80° to 230° C. and preferably from 140° C. to 210° C., this second step leads to the crystallized solid being obtained, which is separated,
c) in a third step, heating the solid obtained at the end of step (b) to a temperature greater than 400° C. so as to eliminate, by decomposition and possibly by combustion if the treatment is carried out in the presence of oxygen, the organic species provided by the structuring agent, and contained in the solid after synthesis.

The pH below 10 of the reaction medium can be obtained either directly from one or more of the products constituting the reaction medium, or by addition to said medium of an acid, a base, an acid salt, a basic salt or a complementary buffer mixture.

The fluoride anions $F^-$ can be introduced into the reaction medium in the form of fluorides, such as sodium fluoride (NaF), ammonium fluoride ($NH_4F$), ammonium hydrogen fluoride ($NH_4HF_2$), tetrapropylammonium fluoride [$(C_3H_7)_4PF$], or hydrolyzable compounds able to release fluoride anions in water, such as silicon fluoride $SiF_4$ or sodium fluorosilicate $Na_2SiF_6$.

Ammonium fluoride or ammonium hydrogen fluoride are preferred salts, as they allow a zeolite having a MFI structure to be obtained that can be easily transformed into its protonated form without having to carry out ion-exchange reactions.

Many sources of silica can be used in the formation of the reaction medium, including:
silicas in the form of hydrogels, aerogels, colloidal suspensions,
silicas resulting from the precipitation of solutions of soluble silicates, or from the hydrolysis of silicic esters such as the tetraethyl ester of monoorthosilicic acid [$Si(OC_2H_5)_4$], or from complexes such as sodium fluorosilicate ($Na_2SiF_6$) or ammonium fluorosilicate [$(NH_4)_2SiF_6$],
silicas prepared by extraction or activation processes of natural or synthetic crystallized compounds, such as aluminium silicates, aluminosilicates, clays, etc. . .

The silicas used can be divided or aggregated.

Usable alumina sources include aluminium salts (sulfates, nitrates, chlorides, fluorides, and acetates for example), aluminium hydroxides and oxides, aluminates, esters such as the tripropyl ester of monoorthoaluminic acid [$Al(OC_3H_7)_3$].

Instead of starting with separate sources of alumina and silica, sources in which the two oxides are combined can also be used, such as, for example, amorphous alumina-silica gels, crystallized aluminosilicates, including clays and zeolites.

The sources of silica and alumina can be used in soluble or solid form, as well as in the form of aggregates such as extrudates or pellets. The latter conditioning is suitable for already aggregated crude or modified zeolite-based sources which can then be transformed, according to the new process, into preformed zeolites.

The sources of the structuring agent able to provide organic cations are preferably tetrahydrocarbylammonium and tetrahydrocarbylphosphonium cations, the hydrocarbyl advantageously being an alkyl, preferably propyl.

The tetrapropylammonium cations (TPA+) or tetrapropylphosphonium cations (TPP+) which are the preferred structuring agents are preferably added in the form of their salts, for example, bromides, fluorides, but they can also be generated in situ from tripropylamine or tripropylphosphine and a propyl halide.

The acids or acid salts, bases or basic salts possibly added in complement to adjust the pH of the reaction medium to the desired value can be chosen from commonly used acids such as hydrofluoric acid (HF), hydrochloric acid (HCl), nitric acid ($NHO_3$), sulfuric acid ($H_2SO_4$), acetic acid ($CH_3COOH$), or acid salts such as ammonium hydrogen fluoride ($NH_4HF_2$), potassium hydrogen fluoride ($KHF_2$), sodium hydrogen sulfate ($NaHSO_4$), potassium hydrogen sulfate ($KHSO_4$), sodium hydrogen phosphate ($NaH_2PO_4$) and commonly used bases such as ammonium hydroxide ($NH_4OH$), soda (NaOH), potash (KOH) or commonly used basic salts such as sodium hydrogen carbonates ($NaHCO_3$) or neutral sodium carbonates ($Na_2CO_3$), sodium acetate ($CH_3COONa$), neutral sodium sulfide ($Na_2S$) or sodium hydrogen sulfide (NaHS) or buffer mixtures such as acetic acid ($CH_3COOH$-sodium) acetate ($CH_3COONa$), ammonium hydroxide ($NH_4OH$)-ammonium chloride ($NH_4Cl$).

The morphology, size and kinetics of the formation of zeolite crystals obtained according to the process of the invention may be modified by the introduction into the reaction medium of additional salts such as sodium chloride (NaCl), potassium chloride (KCl), ammonium chloride ($NH_4Cl$), sodium sulfate ($Na_2SO_4$) and/or crystals optionally of solid compounds related to the zeolites prepared by the process of the invention.

TABLE I

Characteristics of the X-ray diffraction spectrum of the zeolites having a MFI structure according to the invention

| $d_{hkl}$ (Å) ($10^{-10}$ m) | I/Io | $d_{hkl}$ (Å) ($10^{-10}$ m) | I/Io | $d_{hkl}$ (Å) ($10^{-10}$ m) | I/Io |
|---|---|---|---|---|---|
| 11.08–11.26 | FF | 4.06–4.10 | ff | 2.772–2.793 | ff |
| 9.94–10.20 | mf | 3.99–4.05 | f | 2.725–2.749 | ff |
| 9.68–9.90 | f | 3.83–3.89 | F | 2.677–2.697 | ff |
| 8.98–9.08 | ff | 3.80–3.86 | m | 2.648–2.670 | ff |

TABLE I-continued

Characteristics of the X-ray diffraction spectrum of the zeolites having a MFI structure according to the invention

| $d_{hkl}$ (Å) ($10^{-10}$ m) | I/Io | $d_{hkl}$ (Å) ($10^{-10}$ m) | I/Io | $d_{hkl}$ (Å) ($10^{-10}$ m) | I/Io |
|---|---|---|---|---|---|
| 8.00–8.09 | ff | 3.74–3.78 | mf | 2.605–2.619 | ff |
| 7.40–7.52 | ff | 3.70–3.74 | mf | 2.581–2.597 | ff |
| 7.03–7.22 | ff | 3.63–3.67 | mf | 2.545–2.557 | ff |
| 6.64–6.84 | f | 3.58–3.62 | ff | 2.508–2.526 | ff |
| 6.30–6.42 | f | 3.46–3.50 | ff | 2.479–2.50 | ff |
| 5.95–6.07 | f | 3.42–3.46 | f | 2.407–2.419 | ff |
| 5.67–5.79 | f | 3.38–3.42 | ff | 2.393–2.401 | ff |
| 5.54–5.61 | f | 3.33–3.37 | f | 2.326–2.340 | ff |
| 5.32–5.42 | ff | 3.29–3.33 | ff | 2.314–2.332 | ff |
| 5.10–5.23 | ff | 3.23–3.27 | ff | 2.195–2.209 | ff |
| 5.01–5.08 | f | 3.16–3.20 | ff | 2.104–2.120 | ff |
| 4.95–5.03 | f | 3.12–3.16 | ff | 2.077–2.095 | ff |
| 4.84–4.93 | ff | 3.08–3.12 | ff | 2.070–2.084 | ff |
| 4.59–4.64 | ff | 3.03–3.07 | f | 2.004–2.022 | f |
| 4.44–4.50 | ff | 2.976–3.020 | f | 1.985–2.005 | f |
| 4.34–4.40 | f | 2.943–2.962 | f | 1.944–1.964 | ff |
| 4.23–4.29 | f | 2.855–2.881 | ff | 1.007–1.022 | ff |

FF = very strong;
F = strong;
mF = medium to strong;
m = medium;
mf = medium to weak;
f = weak;
ff = very weak.

The solids obtained by the synthesis procedure described hereinabove are zeolites having a MFI structure whose X-ray diffraction diagrams have the characteristics corresponding to the specifications in table I. These zeolites of MFI structure have the following approximate chemical formula, after calcination, expressed in the form of the oxides:

$$M_{2/n}O, Al_2O_3, xSiO_2$$

wherein x can range from 12 to 1000 and wherein M represents the cation(s) for compensation of valence n. The important point is that these solids contain, after the synthesis step as well as after the elimination of organic compounds step, fluorine. Fluorine content in the zeolite determined by elementary analysis ranges, for calcined solids, i.e. those resulting from step (c) described hereinabove, from 0.02 to 1.5% by weight, advantageously from 0.1 to 1.0% and preferably from 0.2 to 0.8%.

The presence of fluorine in zeolites having a MFI structure prepared according to the invention confers properties, namely acid and ion-exchange properties, that are completely different from those of zeolites having a MFI structure synthesized according to conventional processes, i.e., in an alkaline medium (U.S. Pat. No. 3,702,886 for example). After synthesis and elimination of organic compounds by calcination (steps a, b, c), the solids according to the invention are characterized by an infrared-vibration spectrum which shows, as can be seen from the figure, for fluorine contents of 0.8% (curve 1), 0.2% (curve 2) and 0.05% (curve 3) bands conventionally attributed to Si—OH groups (3730–3750 cm$^{-1}$ region) and Al—OH structural groups (3580–3640 cm$^{-1}$ region) and Al—OH structural groups (3580–3640 cm$^{-1}$ zone) that are very weak in comparison with those of a zeolite having a conventional MFI structure, with the same Si/Al ratio of 22 (curve 4% F=0).

The absence or amlost total absence of Al—OH structural groups in the zeolites according to the invention is confirmed by the ion-exchange capacities of these solids. In fact, the ion-exchange capacities of cations such as, for example, Na$^+$, K$^+$, Ga$^{3+}$, Pt(NH$_3$)$_4^{2+}$ etc are very much lower than the theoretical total ion-exchange capacities, calculated from the aluminium content of the crystalline framework.

These solids not having any, or very few, structural hydroxyls and whose exchange capacity is much reduced surprisingly possess remarkable acid properties. Thus, thermodesorption of ammonia which allows the overall acidity of a solid to be estimated (number and strength of the different types of acid sites) shows that solids comprising fluorine incorporated into the structure are very acidic. The thermodesorption spectra of ammonia are comparable to those which would be obtained with zeolites having a conventional MFI structure, whereas the acidity of the solids according to the invention is of a different kind.

Without putting forward a particular theory, it can be proposed that the solids have, in place of at least a part of the conventional Al—(O)—Si≡ sites, sites of the kind:

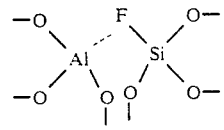

The precise nature of the acid sites present in the solids according to the invention remains to be clarified, whereas it is clear that these sites are essentially linked to the presence of fluorine and are different in nature from the acid sites of zeolites having a conventional MFI structure.

The introduction of fluorine into zeolites is a method which has already been suggested to increase the acidity of these solids (J. MIALE and C. CHANG U.S. Pat. No. 4,540,841). However, in the prior art, fluorine is introduced into the zeolite by modifications carried out after synthesis. In other words, conventional synthesis is carried out, i.e. in an alkaline medium, then the solid is treated by a technique which, in principle, allows the fixation of fluorine. These previously suggested techniques generally have a large number of drawbacks. For example, as is the case when the solid is treated with gaseous fluorine, they are likely to lead to a degradation in crystalline order (U.S. Pat. No. 4,297,335). In the present preparation of the catalyst, fluorine is introduced into the zeolite at the level of synthesis and, to the contrary, allows extremely well crystallized solids to be obtained.

By using special processes, it is possible to partially or totally eliminate the fluorine contained in the solids entering into the composition of the catalysts according to the invention without altering their crystallinity. One technique for the defluorination of the solids consists in carrying out a treatment in an ammoniacal solution at temperatures ranging from room temperature to 200° C. (treatment in the autoclave under autogenous pressure). The partial or total elimination of fluorine leads:

on the one hand, as indicated hereinabove, to the appearance of two bands situated around 3740 and 3608 cm$^{-1}$ on the IR spectrum corresponding, according to the attributions permitted in scientific literature, to terminal silanol groups and structural Al—OH groups respectively and on the other hand, to restoration of the ion-exchange capacity as calculated from the aluminium content of the framework of the solids.

Thus, depending on the defluorination treatment, solids containing a large number of Al—OH and Si—OH groups, as well as varying ion-exchange capacities can be obtained for the same Si/Al ratio of the framework. A partially defluorinated solid thus contains, in addition to conventional Al—OH type acid sites acting as exchange sites, special acid sites whose exact nature has not yet been completely elucidated but which unquestionably result from the introduction of fluorine into the solids during synthesis.

It is this characteristic of the solids that was taken advantage of to prepare containing-gallium catalysts and likely, for example, to aromatize a hydrocarbon such as propane and, more generally, a $C_{2-4}$- light-gas cut in the optionally presence of olefins.

The present invention thus relates to an aluminosilicate type catalyst characterized by the following composition expressed by weight:
a) 0.01 to 1.0% by weight of gallium, preferably 0.03 to 4%;
b) 0.1 to 99.49% of a matrix chosen from the group formed by alumina, silica, magnesia, a clay and any combination of at least two of the above-mentioned compounds and
c) 0.50 to 99.99% of a zeolite synthesized in a fluorine medium usually having the following approximate chemical formula:

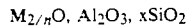

wherein
M represents a proton and/or a metallic cation,
n is the valence of said cation,
x is a number ranging from 12 to 1000 ($SiO_2Al_2O_3$ molar ratio)
The zeolite has a fluorine content ranging from 0.02 to 1.5% by weight, preferably from 0.1 to 1% by weight, the fluorine being incorporated during synthesis, said zeolite also being characterized by the X-ray diffraction given diagram in table I.

After synthesis in a fluorine medium, the solid can, if need be, be submitted to a defluorination process allowing its ion-exchange capacity to be adjusted to the gallium content to be introduced. The more fluorine content is reduced, the more gallium content can be increased.

Defluorination treatment is more or less severe depending on the level of defluorination desired. It consists of one or more successive treatments of the solid under reflux in an ammonium hydroxide solution having a normality ranging from 0.05 to 5N and preferably from 0.1 to 3N, for a period of time ranging from about 0.5 to 5 hours and preferably from 1 to 4 hours with a V/W ratio, defined as the volume of solution to dry solid weight, ranging from about 5 to 50 $cm^3g^{-1}$ and preferably from 10 to 30 $cm^3g^{-1}$. The solid, after each washing, is then abundantly washed with distilled water and dried in an oven. After these treatments and depending on their severity, the fluorine content of the solid ranges from 0.9 to 0.01% by weight. If practically all the fluorine is eliminated by repeated treatment, solids are again obtained which are distinguished, in particular, by their IR spectrum in the region of 3800-3500 $cm^{-1}$ of zeolites having a conventional MFI structure with the same Si/Al ratio of the framework:

the solids contained in the catalyst according to the invention have a larger proportion of Si—OH groups.

The partially or totally defluorinated solid can be submitted as such to deposit of gallium, or shaped according to any of the techniques known to the man skilled in the art. In particular, it can be mixed with a generally amorphous matrix, for example, a wet alumina gel powder. The mixture is then shaped, for example by extrusion through a die. The zeolite content of the support thus obtained generally ranges about 0.5 to 99.99% and advantageously from about 40 to 90% in weight. More particularly, it ranges from about 60 to 85% by weight with respect to the zeolite and matrix. Catalyst content of the matrix advantageously ranges from about 10 to 60% and preferably from about 15 to 40% by weight. Shaping can be carried out using matrices other than alumina such as, for example, magnesia, silica alumina, natural clays (kaolin, bentonite), and by techniques other than extrusion such as pelleting or coating. Gallium is then deposited on the support by any of the processes known to one of ordinary in the art which allows the deposit of the metal in zeolite. The cationic exchange technique with competition can be used in which the competing agent is preferably ammonium nitrate or even the technique for deposit of gallium on the catalyst by impregnation. The gallium exchange or impregnation solutions can be prepared from gallium compounds such as, for example, gallium oxide, gallium nitrate, gallium sulfate, gallium halides or gallium hydroxide. These ion-exchange or impregnation techniques can also be used to directly deposit the metal on the zeolite powder, before its possible mixing with a matrix. Content of gallium deposited on the catalyst at the end of the ion-exchange and/or impregnation step(s) depends on the fluorine content of the solid; it is between 0.01 and 10% by weight with respect to the catalyst and preferably between 0.03 and 4.0% by weight.

The catalyst of the present invention, obtained by the previous procedures, is used for the aromatization reaction of light gases, for example, propane and/or a $C_{2-4}$- mixture in the optionally presence of olefins. This reaction is of particular interest as it increases the value of the residues of refining processes into products of greater value (benzene, toluene, xylenes) while contributing to the production of large amounts of hydrogen required for hydrotreatment processes for example.

The charge containing butane and/or propane and/or ethane, in the optionally presence of olefins, is contacted with the catalyst of the present invention at a temperature ranging from 400° to 700° C., and more particularly, from 500° to 600° C.

The following examples describe the invention without in any way limiting its scope, they are given for a charge uniquely comprised of propane but can be easily adapted to a more complex charge comprised of a mixture of $C_{2-4}$- light gases in the presence of olefins.

All the catalysts used in the following example contain 20% of a matrix and 80% of zeolite.

EXAMPLE 1

Preparation of zeolites A and B entering into the composition of the catalyst according to the invention.

Two zeolites having an MFI structure with Si/Al atomic ratios ranging from 25 to 150 are prepared from a single aluminium and silica source, that is, partially dealuminated Tixolex 28 and using two different F/Si atomic ratios in the two reaction mixtures.

Tixolex 28 is a sodium aluminosilicate marketed by Rhône Poulenc and characterized by the atomic ratios Si/Al=7.3 and Na/Al=1.1. The partially dealuminated form is prepared as follows: 60 g of Tixolex 28 are stirred for 3 hours at room temperature with 600 ml of 2M $HNO_3$. The product obtained is filtered and washed with water to pH 7. After drying at 80° C., it is stored under a relative humidity of 80%. The weight composition is as follows: 76.10% $SiO_2$; 5.46% $Al_2O_3$; 0.24% $Na_2O$; 17.63% total $H_2O$.

Two reaction mixtures A and B, whose molar and weight compositions are given in table 2, are prepared. In order to do this, the mixture of $NH_4F$, $N(C_3H_7)_4^+$ $Br^-$ and water is added to the partially dealuminated Tixolex. The crystallization of the two reaction mixtures (A, B) is carried out in two autoclaves, whose internal coating consists of polytetrafluoroethane, at 190° C. for 3.5 days.

TABLE 2

| | Partially dealuminated Tixolex | | $NH_4F$ | $N(C_3H_7)_4$ Br | $H_2O$ |
|---|---|---|---|---|---|
| | $SiO_2$ | $Al_2O_3$ | | | |
| A moles | 0.2 | 0.0084 | 0.04 | 0.1 | 1.6 |
| g | 15.8 | | 1.48 | 26.6 | 28.8 |
| B moles | 0.2 | 0.0084 | 0.25 | 0.1 | 1.6 |
| g | 15.8 | | 9.25 | 26.6 | 28.8 |

After calcination, the solids are filtered and washed with a 10% diethylamine solution, then with hot water. The solids are then dried at 80° C. Crystallographic analysis shows that products A and B are zeolites having a MFI structure whose X-ray diffraction diagram corresponds to the specifications given in table 1. Chemical analysis of products A and B after calcination under air at 550° C. is as follows:

| Products | A | B |
|---|---|---|
| Molar $SiO_2/Al_2O_3$ | 56 | 280 |
| F (% weight) | 0.8 | 0.5 |

EXAMPLE 2

Catalyst B1 conforming with the invention.

Solid B of example 1 is shaped by extrusion with an alumina-type binding agent or matrix in a proportion of 80% by weight of zeolite and 20% by weight of binding agent.

Catalyst B1 is prepared as follows: a pseudo-boehmite alumina supplied by CONDEA Ltd. is peptized by addition of nitric acid then mixed.

Catalyst B1 is obtained by mixing this pseudo-boehmite with zeolite B.

This zeolite is introduced in a proportion of 80 g of zeolite per 20 g of binding agent then mixed; the paste obtained, after adjustment of its consistency by the addition of small amounts of water, is passed through a die having a diameter of 1.4 mm, then dried under a stream of air at 120° C. and calcined at 550° C. for one hour.

The gallium is deposited on the extrudates by ion-exchange with competition. The exchange solution is prepared from gallium nitrate $Ga(NO_3)_3$ with ammonium nitrate $NH_4NO_3$ as the competing agent. The competition ratio is about 10. The pH of the gallium solution is adjusted to 2 with ammonium hydroxide.

As the starting solid B has a large fluorine content (0.5% in weight), the gallium content achieved after three successive exchanges is appreciably comparable to that of example 1. Catalyst B1 is tested for the aromatization of propane at 600° C., under atmospheric pressure. The propane is diluted in argon in a volume ratio of 20% propane per 80% argon. The catalytic performance is reported in table 3.

It is defined by:

(conversion of propane % wt) = 100 ×

(weight of propane in the charge) − (weight of products recovered)/(weight of propane in the charge)

(selectivity in B, T, X % wt) = 100 ×

(weight of B + T + X recovered)/(weight of propane in the charge) − (weight of products recovered)

(yield in aromatic products % wt) = 100 × (weight of

B + T + X recovered)/(weight of propane in the charge)

EXAMPLE 3

Catalyst B2.

This example illustrates the importance of fluorine in the catalytic properties of the aromatization of propane.

Zeolite B of example 1 is used as the starting zeolite. The fluorine content of 0.5% after decomposition of structuring cations is adjusted to 0% by defluorination in ammoniacal medium, according to the procedure described below:

The zeolite is submitted to 3 cycles:
+ 0.2N $NH_4OH$ solution at 140° C. for 4 hours
+ filtration and washing with distilled water
+ drying in the oven at 150° C.

After treatment, a solid is obtained whose crystallinity and Si/Al ratio are unaltered but whose fluorine content is about 0%. Gallium is then introduced (2.45% weight), according to the procedure described in example 2, then the solid is shaped with a binding agent according to the description in the same example. Catalyst B2 is tested for the aromatization of propane. The results obtained are reported in table 3.

It can be seen that elimination of fluorine has allowed an increase in the exchange capacity of the zeolite and thus an increase in the amounts of gallium introduced, but this occurs to the detriment of the acid properties and thus of catalytic performance. The solid B2 is much less active and selective in B, T, X than catalyst B1.

EXAMPLE 4

Catalyst A1 of the present invention.

This example shows that the ion-exchange capacity of the zeolite can be adjusted by partial elimination of fluorine while keeping the acid properties special to the solids of the present invention.

Zeolite A of example 1 is used as the starting zeolite. The initial proportion of fluorine of zeolite A after calcination of structuring cations is adjusted to 0.2% by defluorinating treatment in 0.1N ammoniacal medium at 100° C. for 4 hours. After treatment, the solid is charged with gallium and shaped according to the procedure in example 2. Catalyst A1, which contains 0.55% weight of gallium and 0.2% of fluorine with a SiO$_2$/Al$_2$O$_3$ ratio of 56, is tested in a propane aromatization reaction. On observation of the results reported in table 3, it can be seen that partial elimination of fluorine has led to an increase in the ion-exchange capacity of the zeolite, thus allowing introduction of much larger amounts of gallium while preserving a fluorine content sufficient for preservation of the special acid properties of the catalysts of the present invention and, thus, good catalytic performances in the aromatization of propane.

EXAMPLE 5

Comparison catalyst C1 (non-conforming with the invention).

Zeolite C is an MFI structure zeolite synthesized in conventional basic medium, described in U.S. Pat. No. 3,702,886. This zeolite is synthesized with a Si/Al ratio of 240 and does not contain fluorine. After calcination of structuring cations at 550° C. followed by three exchanges in 3N NH$_4$NO$_3$ medium, the deposit of gallium is carried out in conformity with the description in example 2, i.e. by exchange. Gallium content is equivalent to that of catalyst A1. The solid is shaped under the same conditions as those described in example 2 then tested for aromatization of propane. The results are reported in table 3.

It is observed that in the absence of fluorine, catalyst C1 is much less active and selective in aromatic products than the catalysts of the present invention.

EXAMPLE 6

Comparison catalyst C2 (non-conforming with the invention).

The starting zeolite is the conventional zeolite C of example 5. This zeolite then undergoes calcination at 550° C. followed by three exchanges in 3N NH$_4$NO$_3$ medium. The solid is then submitted to treatment at 450° C. for 4 hours under an atmosphere containing CH$_3$F. The fluorine content achieved at the end of this treatment is 0.20% by weight. Gallium is then introduced and the solid is shaped according to the conditions described in example 2 (i.e. by exchange). Catalyst C2 is tested for aromatization of propane. It appears that at a fluorine content equivalent to that of catalyst A1, catalyst C2 shows poor catalytic performance in comparison with the catalysts of the present invention.

TABLE 3

| CATALYST | A1* | B1* | B2** | C1*** | C2*** |
|---|---|---|---|---|---|
| Si/Al | 28 | 140 | 140 | 240 | 240 |
| % Ga | 0.55 | 0.15 | 2.45 | 0.55 | 0.36 |
| % F | 0.2 | 0.5 | 0 | 0 | 0.20 |
| PPH | 2.1 | 0.8 | 0.9 | 1.1 | 1.1 |
| Propane conversion | 72.0% | 41.3% | 37.0% | 21.3% | 5.8% |
| B, T, X yield | 37.4% | 19.4% | 15.1% | 2.6% | 0.8% |
| B, T, X selectivity | 52.0% | 47.1% | 41.0% | 12.1% | 14.6% |

*Zeolite according to the invention
**Zeolite according to the invention but completely defluorinated
***Conventional MFI zeolite

We claim:
1. A catalyst contaiing by weight:
   a) 0.01 to 10% of gallium,
   b) 0.1 to 99.49% of a matrix chosen from the group consisting of alumina, silica, magnesia, a clay and all combinations of at least two of the compounds mentioned hereinabove,
   c) 0.50 to 99.99% of a zeolite synthesized in fluorine-containing medium, with an SiO$_2$/Al$_2$O$_3$ molar ration ranging from 12 to 1000, said zeolite having a fluorine content of from 0.02 to 1.5% by weight, the fluorine being incorporated during the synthesis of said zeolite, said zeolite having an X-ray diffraction diagram conforming with table 1.
2. A catalyst according to claim 1 containing 0.03 to 4% by weight of gallium.
3. A catalyst according to claim 1 wherein said zeolite shows two bands in its IR spectrum situated around 3730–3750 cm$^{-1}$ and 3580–3640 cm$^{-1}$ corresponding to terminal silanol groups and structural Al—OH groups respectively.
4. A catalyst according to claim 1 wherein said matrix is an alumina.
5. A catalyst according to claim 3, containing 0.03–4% by weight of gallium.
6. A catalyst according to claim 1, wherein the fluorine content of the zeolite is 0.1–1%.
7. A catalyst according to claim 1, wherein the fluorine content of the zeolite is 0.2–0.8%.
8. A catalyst according to claim 1, wherein the zeolite content is 40–90% by weight.
9. A catalyst according to claim 1, wherein the zeolite content is 60–85% by weight.
10. A catalyst according to claim 9, wherein the fluorine content is 0.2–0.8%.

* * * * *